United States Patent [19]

Nakajima et al.

[11] Patent Number: 4,503,147

[45] Date of Patent: Mar. 5, 1985

[54] MONOMETHYLAMINE-OXIDIZING ENZYME

[75] Inventors: Motoo Nakajima; Kazuo Nakamura; Yoshio Shirokane; Kiyoshi Mizusawa, all of Noda, Japan

[73] Assignee: Kikkoman Corporation, Noda, Japan

[21] Appl. No.: 435,316

[22] Filed: Oct. 19, 1982

[30] Foreign Application Priority Data

Oct. 22, 1981 [JP] Japan ................................ 56-167910
Oct. 22, 1981 [JP] Japan ................................ 56-167911

[51] Int. Cl.$^3$ .......................... C12Q 1/26; C12N 9/06; C12R 1/05; C12R 1/07
[52] U.S. Cl. ...................................... 435/25; 435/191; 435/829; 435/832
[58] Field of Search .............................. 435/25, 191

[56] References Cited

PUBLICATIONS

Memoirs of the Research Institute for Food Science, vol. 27, pp. 1–13 (1966).

*Primary Examiner*—Lionel M. Shapiro
*Attorney, Agent, or Firm*—Banner, Birch, McKie & Beckett

[57] ABSTRACT

A monomethylamine-oxidizing enzyme can be obtained by cultivating in a medium a strain which belongs to Genus Bacillus and has an ability to produce a monomethylamine-oxidizing enzyme. This enzyme exhibits several beneficial properties including the ability to oxidatively deaminate the amino group of monomethylamine to produce formaldehyde, ammonia, and hydrogen peroxide. The enzyme exhibits a high substrate specificity for monomethylamine, ethylamine, and n-proplyamine while showing no substrate specificity for benzylamine, dimethylamine, trimethylamine, ethylenediamine and tryamine. In addition, the enzyme is stable through an elevated temperature range permitting faster reaction rates and therefore a shorter overall quantitative evaluation. Another property includes a low Km value which allows smaller quantities of the enzyme to be employed per sample.

14 Claims, 8 Drawing Figures

CONTENT OF MONMETHYLAMINE

FIG. 8

CONTENT OF METHYLGUANIDINE

MONOMETHYLAMINE-OXIDIZING ENZYME

This invention relates to a novel monomethylamine-oxidizing enzyme, a process for manufacturing said enzyme and a method for quantitatively determining monomethylamine by the use of said enzyme.

With respect to amine-oxidizing enzymes, it is reported that strains belonging to *Aspergillus niger, Penicillum chrsogenum, Monascus anka* and *Fusarium bulbigenum* produce amine-oxidizing enzymes (Agr. Biol. Chem, Vol. 29, No. 2, p. 117 to 123, 1965).

None of these known amine-oxidizing enzymes, however, shows enzymatic activity to monomethylamine.

Hence, the present inventors conducted various stuies and found that there can be obtained a monomethylamine-oxidizing enzyme having an extremely high substrate specificity toward monomethylamine by cultivating a strain belonging to Genus Bacillus in a medium and extracting from the culture mixture. Also, the inventors found that, by causing said monomethylamine-oxidizing enzyme to act upon a sample of which monomethylamine content is to be determined and then measuring the quantity of formaldehyde, ammonia or hydrogen peroxide formed, monomethylamine can be quantitatively determined by a very simple procedure, in a short time and with a very excellent sensitivity. Thus, the present invention has been accomplished.

An object of this invention is to provide a novel monomethylamine-oxidizing enzyme and a process for manufacturing said enzyme.

Another object of the invention is to provide a method for quantitatively determining monomethylamine by the use of said enzyme.

Other objects and advantages of this invention will be apparent from the descriptions given below.

In the accompanying drawings.

Physical and chemical properties of the novel monomethylamine-oxidizing enzyme provided by the present invention will be described in detail together with measurement methods of these properties.

(1) Action

This enzyme, similarly to known amine-oxidizing enzymes, oxidatively deaminates monoamines in the presence of water and oxygen to produce aldehydes, ammonia and hydrogen peroxide, and exhibits an extremely high substrate specificity toward monomethylamine. When this enzyme is allowed to act upon a monomethylamine substrate, as shown in the following reaction formula, 1 mole of monomethylamine requires 1 mole of water and 1 mole of oxygen, and each 1 mole of formaldehyde, ammonia and hydrogen peroxide is formed.

$$CH_3NH_2 + H_2O + O_2 \rightarrow HCHO + NH_3 + H_2O_2$$

(2) Enzyme activity measurement

Monomethylamine hydrochloride as substrate is dissolved into 0.1 M $KH_2PO_4$-$Na_2B_4O_7$ buffer solution (pH 7) and the solution is ordinally adjusted to 1 mM concentration of substrate. To 1.0 ml of this substrate solution, is added 0.1 ml of an enzyme solution diluted with the same buffer solution and the mixture is subjected to reaction for 10 min. at 30° C. By adding 1 ml of 5N KOH solution, the enzymatic reaction is stopped. By this enzymatic reaction, monomethylamine is oxidatively decomposed to produce formaldehyde, ammonia and hydrogen peroxide. Then, to the reaction mixture is added 1 ml of 0.5 N hydrochloric acid solution containing 0.5% 4-amino-3-hydrazino-5-mercapto-1,2,4-triazole (to be abbreviated as AHMT hereinafter) and the mixture is subjected to reaction for 15 min. at 30° C. To the reaction mixture is added 1 ml of 0.2 N potassium hydroxide solution containing 0.75% $KIO_4$ and the mixture is thoroughly stirred to develop a color. The colored solution is poured into a transparent cell and its absorption at 550 nm is measured to quantitatively determine the above produced formaldehyde.

In the expression of activity, a quantity of the monomethylamine-oxidizing enzyme enough to oxidize 1 μmole of monomethylamine per 1 min. under the above measurement condition to produce 1 μmole of formaldehyde is defined as one unit.

(3) Substrate specificity

The purified monomethylamine-oxidizing enzyme was allowed to act upon various substrates shown in Table 1 to measure the enzyme activities toward these substrates. The result indicated that the enzyme of the present invention has a high substrate specificity toward monomethylamine. It was also found that the enzyme of the invention has a very low Km value of $6.2 \times 10^{-5}$ M (pH 9.0) toward monomethylamine and has a high substrate specifically toward monomethylamine and even at a low concentration.

In Table 1, activity of monomethylamine-oxidizing enzyme for each substrate was measured at the substrate concentration of 10 mM, from which each relative activity was calculated by taking that for monomethylamine as 100.

TABLE 1

| Substrate | Relative activity % | Substrate | Relative activity % |
|---|---|---|---|
| Monomethylamine | 100 | Tyramine | 0 |
| Ethylamine | 90 | Histamine | 1 |
| n-Propylamine | 60 | Dimethylamine | 0 |
| n-Butylamine | 18 | Trimethylamine | 0 |

TABLE 1-continued

| Substrate | Relative activity % | Substrate | Relative activity % |
|---|---|---|---|
| n-Amylamine | 19 | Hydroxylamine | 0 |
| n-Hexylamine | 10 | Ethanolamine | 1 |
| Benzylamine | 1 | Diaminomethane | 16 |
| i-Propylamine | 0 | Ethylenediamine | 0 |
| i-Butylamine | 2 | Putrescine | 0 |
| Agmatine | 1 | | |

(4) Optimum pH range

Figure 1:
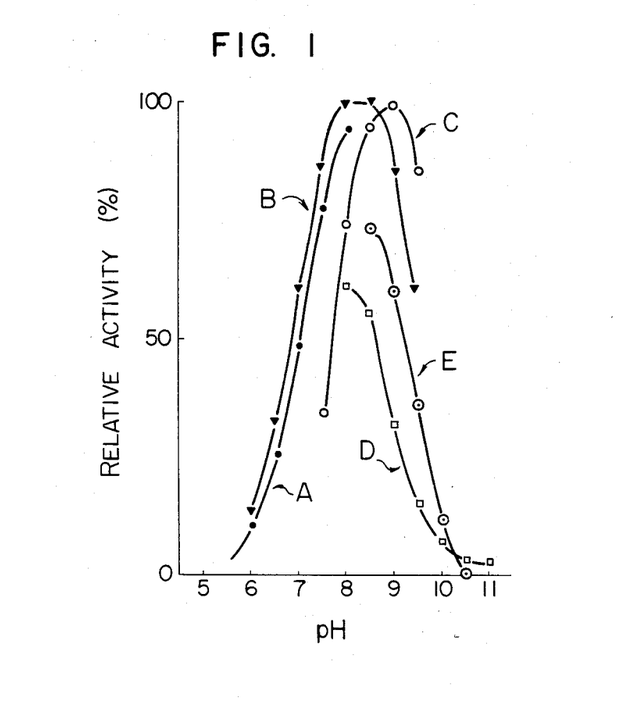
FIGS. 1 to 4 are curves respectively showing the optimum pH, the pH stability, the thermal stability and the optimum action temperature range of the monomethylamine-oxidizing enzyme.

Enzymatic activities of the monomethylamine-oxidizing enzyme toward monomethylamine at various pH levels were measured by using 0.1 M $KH_2PO_4$-$Na_2HPO_4$ buffer solution (pH 5.5 to 8.0), 0.1 M $KH_2PO_4$-$Na_2B_4O_7$ buffer solution (pH 6.0 to 8.5), 0.1 M Veronal buffer solution (pH 7.5 to 9.5), 0.1 M $H_3BO_4$-KCl-$Na_2CO_3$ buffer solution (pH 8.0 to 11.0) and 0.1 M $Na_2CO_3$-$NaHCO_3$ buffer solution (pH 8.5 to 10.5). As shown in FIG. 1, the optimum pH was confirmed to be in the range of 8 to 9.

(5) Stable pH range

Figure 2:
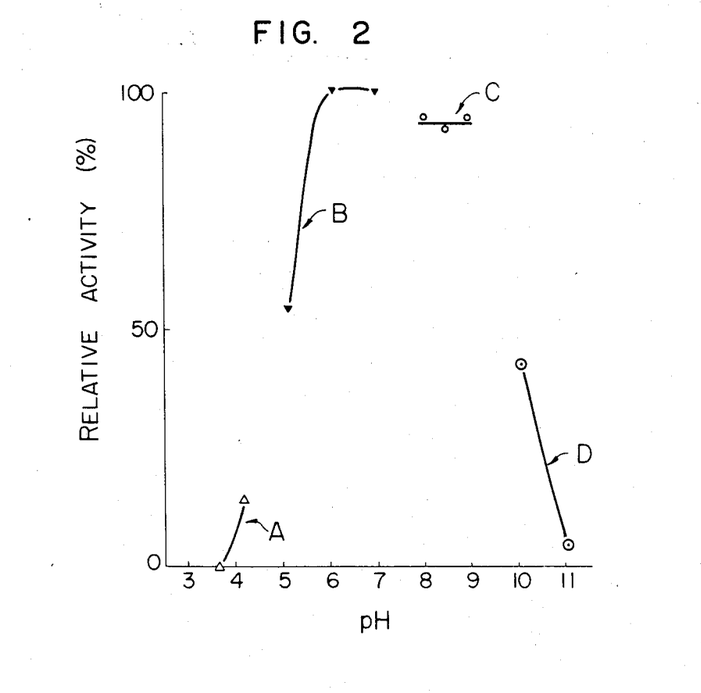

Enzymatic activities of the monomethylamine-oxidizing enzyme at various pH levels from 3.5 to 11 were measured after keeping the enzyme for 30 min. at 30° C. in each of 0.1 M acetic acid buffer solutions (pH 3.5, 4.0), 0.1 M $KH_2PO_4$-$Na_2B_4O_7$ buffer solutions (pH 5.0, 6.0, 7.0, 8.0, 9.0), 0.1 M Veronal buffer solutions (pH 8.0, 8.5, 9.0) and 0.1 M $Na_2CO_3$-$NaHCO_3$ buffer solutions (pH 10.0, 11.0). As shown in FIG. 2, the stable pH was confirmed to be in the range of 6 to 9.

(6) Thermal stability

Figure 3:
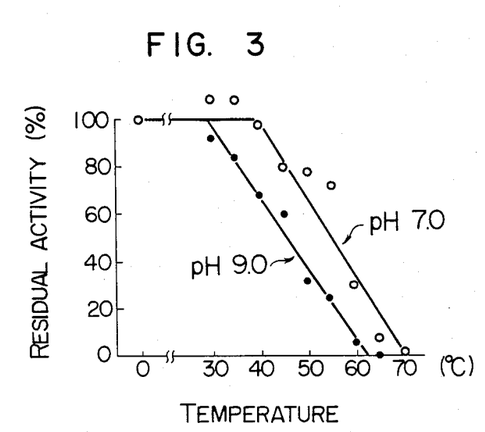

After the enzyme of the present invention had been treated for 10 min. at various temperatures at pH 7.0, the residual activity of the enzyme was measured against 1 mM of a monomethylamine solution as substrate. As shown in FIG. 3, the enzyme is completely inactivated at a temperature of 70° C. or above. At pH 9.0, the enzyme is completely inactivated at a temperature of 63° C. or above.

(7) Optimum action temperature range

Figure 4:
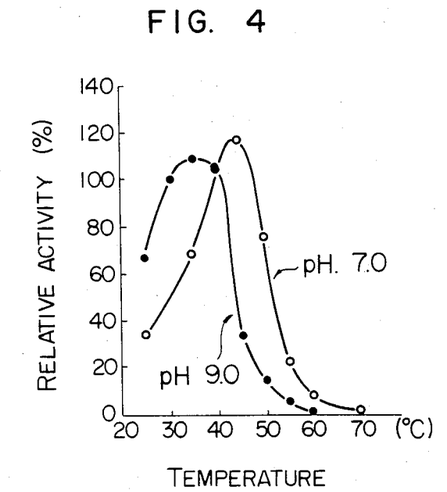

The pH of a reaction system was fixed at 7.0 by the use of 0.1 M $KH_2PO_4$-$Na_2B_4O_7$ buffer solution and activities of the enzyme of the present invention at various temperatures were examined. Also, the pH of the reaction system was fixed at 9.0 by the use of 0.1 M Veronal buffer solution and enzymatic activities at various temperatures were examined. As shown in FIG. 4, the optimum action temperature range was confirmed to be from 40° to 50° C. at pH 7 and from 30° to 40° C. at pH 9.

(8) Inactivating pH condition

At 30° C., the monomethylamine-oxidizing enzyme is completely inactivated at pH 3.0 or below and pH 12 or above.

(9) Inhibition

Residual activities of this enzyme after 10 min. treatment at 30° C. at pH 9 in the presence of 5 mM of KCN, 5 mM of 8-oxyquinoline, 5 mM of O-phenanthroline and 5 mM of sodium diethyldithiocarbamate were 5.7, 34.0, 70.9 and 59.3%, respectively, wherein the enzymatic activity in the absence of inhibitor was taken as 100. Residual activities of this enzyme after the same treatment in the presence of 1 mM of $HgCl_2$, 1 mM of p-chloromercuribenzoic acid, 1 mM of monoiodoacetic acid, 1 mM of iodoacetamide and 1 mM of semicarbazide hydrochloride were 0, 0.7, 34.0, 2.2 and 0%, respectively.

(10) Stabilization

The enzyme is stabilized by adding 2% (w/v) of saccharose thereto.

(11) Method of purification

Wet bacterial cells are collected by centrifuging the culture mixture. The bacterial cells are suspended in 0.01% lysozyme—0.01 M phosphate buffer solution (pH 7.0) and subjected to bacteriolysis for 1 hr. at 37° C. Then, 0.4% aqueous ethyleneimine polymer solution is added in a quantity of 2.5% and the precipitate formed is removed by centrifugation to obtain a supernatant (crude enzyme solution). This crude enzyme solution is salted out with ammonium sulfate to obtain a precipitate fraction from 0.35 saturation to 0.5 saturation. This precipitate is dissolved into a small quantity of 0.01 M phosphoric acid buffer solution (pH 7.0) containing 0.5 M KCl, and the solution is subjected to gel filtration chromatography by the use of a column packed with TOYOPEAL HW-55S (hydrophilic vinyl polymer manufactured by Toyo Soda), the same buffer solution and a flow rate of 1 ml/min.

The active fraction obtained is dialyzed against 0.1 M $KH_2PO_4$ - $Na_2B_4O_7$ buffer solution (pH 8) using cellulose acetate film and then is adsorbed with the same buffer solution onto a column packed with ω-aminohexyl agarose (manufactured by Miles Laboratories, Inc.). After the unadsorbed fraction is thoroughly washed out with same buffer, the adsorbed fraction is eluted with the same buffer solution containing 0.2 M KCl according to affinity chromatography. The eluted active fraction, after being dialyzed against 0.001 M phosphoric acid buffer solution (pH 7.0) using cellulose acetate film, is adsorbed onto a column packed with hydroxyapatite (manufactured by Bio-Rad Laboratories, U.S.A.) previously equilibrated with the same buffer solution. By using phosphate buffer of stepwise increased concentrations of 0.01, 0.02, 0.03, 0.04 and 0.05 M, the active fractions of the enzyme of the present invention are collected separately.

These active fractions are dialyzed against deionized water and freeze-dried to obtain purified powders of the enzyme of the present invention.

An electrophoretic measurement revealed that these purified powders are uniform electrophoretically.

(12) Molecular weight

This enzyme has a molecular weight of 320,000 as measured by gel filtration method [P. Andrews (1965) Biochem. J., Vol. 96, 595] using TOYOPEAL HW-55S.

The enzyme of this invention having the above physical and chemical properties can be suitably used for quantitative determination of monomethylamine.

Next, the process for manufacturing the monomethylamine-oxidizing enzyme of this invention will be described specifically.

Bacteria used in the process for manufacturing the enzyme of the present invention may be any strains so far as they belong to Genus *Bacillus* and have an ability to produce the monomethylamine-oxidizing enzyme. They may be any natural strains newly separated, any existing strains under cultivation, and any mutant strains giving the monomethylamine-oxidizing enzyme at a high yield which are obtained by exposing natural strains to a mutagenesis method such as a physical treatment, for instance, an irradiation of ultraviolet light, X-ray or γ-ray, or a chemical treatment by a chemical reagent, for instance, nitrosoguanidine.

*Bacillus* sp. N - 104 separated by the present inventors from the soil of a farm in Noda City, Chiba Prefecture, Japan has an ability to produce the monomethylamine-oxidizing enzyme with a high yield and is particularly suitable for practical use. This bacterium has been deposited in Fermentation Research Institute, Agency of Industrial Science and Technology, Japan as FERM BP-59, in compliance with Budapest Treaty on The International Recognition of the Deposit of Microorganism.

Bacteriological properties of *Bacillus* sp. N - 104 (FERM BP-59) are as follows.

(a) Morphology (1) Shape and size of cell: It is a short bacillus having a size of 1.5 to 2 by 3 to 5 microns.

(2) Polymorphism of cell: There is observed no polymorphism.

(3) Motility: Motile by means of peritrichous flagella.
(4) Spore: It forms spores.
(5) Gram-strain: Positive (b) The state of growth in various media (1) Bouillon-agar plate culture When cultivated at 30° C. for 48 hr., it forms circular colonies having a diameter of 0.5 to 1 mm. Their surfaces are flat and smooth and yellow with a gloss.

(2) Bouillon-agar slant culture

When cultured at 30° C. for 48 hr., it shows a stringly weak growth. The surface is flat with yellow color and gloss.

(3) Bouillon submerged culture

In a standing culture at 30° C. for 48 hr., it gives slight turbidity.

(4) Bouillon-gelatin stab culture

In a standing culture at 20° C. for 42 days, it slowly liquefies gelatin.

(5) Litmus milk culture

In a standing culture at 30° C. for 14 days, no change is seen.

(c) Physiological properties (1) Reduction of nitrates: Observed although slightly.
(2) Denitrification reaction: Positive. There is no gas formation.
(3) MR test: Negative.
(4) VP test: Negative.
(5) Indole formation: Not observed.
(6) Hydrogen sulfide formation: Not observed.
(7) Hydrolysis of starch: Observed although slightly.
(8) Utilization of citric acid: Observed.
(9) Inorganic nitrogen source: Not utilized.
(10) Pigment formation: Not observed.
(11) Urease: Positive.
(12) Oxidase: Negative.
(13) Catalase: Positive.
(14) Growing condition range:
   Temperature: 15° to 44° C.
   pH: 5 to 9.5
(15) Behavior to oxygen: Aerobic.
(16) 0 - F test (Huge Heifson method): Negative.
(17) Utilization of carbon source: Acids are formed from fructose. (18) It assimilates methanol.

By comparing the above mentioned physicochemical properties of *Bacillus* sp. N - 104 (FERM BP-59) with the classification made in "Bergey's Manual of Determinative Bacteriology, 8th Ed.", this bacterium was judged to belong to Genus *Bacillus*, because (a) it forms spores, (b) it is a bacillus, (c) it is aerobic, (d) it has an ability to produce catalase and (e) it is a Gram-positive bacterium. When this bacterium is compared with known bacteria belonging to Genus *Bacillus*, it appears to be similar to *Bacillus cereus, Bacillus anthracis, Bacillus thuringiensis* and *Bacillus megaterium* from the point that its cells are very large (1.5 to $2\mu$ by 3 to $5\mu$), however, it is different from these bacteria in that it does not produce acids from glucose but assimilates methanol. Accordingly, this bacterium was judged to be a new species belonging to Genus *Bacillus*.

Next, cultivating methods and conditions for the bacteria of this invention will be described.

Cultivating methods and conditions for the bacteria for producing the monomethylamine-oxidizing enzyme are not restricted as long as the objects of this invention are not particularly impaired. Accordingly, there can be adopted cultivating methods and conditions which provide environments where the growth of bacteria belonging to Genus *Bacillus* and producing the monomethylamine-oxidizing enzyme as well as the manufacture of the enzyme are possible.

When the wild strain of *Bacillus* sp. N - 104 (FERM BP-59) is used, it has been found that the manufacture of the monomethylamine-oxidizing enzyme is conducted more advantageously in liquid culture than in solid culture. However, by applying an appropriate strain-improving technique to this bacterium, a strain suitable for solid culture will be derived.

In liquid culture, there are considered various media selected from a variety of carbon sources, nitrogen sources and small amount ingredients which are assimilated by the present strain. Addition of 0.01 to 2% (w/v) of monomethylamine hydrochloride to medium significantly increases the yield of the monomethylamine-oxidizing enzyme. As carbon sources, there may be mentioned glucose, glycerol, maltose, soluble starch, methanol, etc. As nitrogen sources, there may be mentioned various amino acids, peptone, soybean powder, hydrolysis products of various proteins, corn steep liquor, meat extracts, yeast extract, sodium nitrate, etc. As small amount ingredients, there may be mentioned sodium salts, potassium salts, manganese slats, magnesium salts, calcium salts, zinc salts, iron salts, phosphates, sulfates, etc.

As specific examples of media, there may be mentioned, for instance, a medium (pH 7.2) containing 1% of glucose, 2% of yeast extract, 0.1% of potassium biphosphate, 0.1% of magnesium sulfate, 0.01% of ferrous sulfate and 0.01% of manganese chloride (hereinafter to be abbreviated as Medium A); a medium containing 0.1% of monomethylamine hydrochloride, 1% of glucose, 1% of yeast extract, 0.1% of potassium biphosphate, 0.05% of magnesium sulfate, 0.01% of ferrous sulfate and 0.01% of manganese chloride (hereinafter to be abbreviated as Medium B); a substitute bouillon medium containing 1% of a meat extract, 1% of a polypeptone and 0.5% of sodium chloride; a malt extract medium containing 2% of malt juice, 2% of glucose and 0.1% of peptone; Sabouraud's medium containing 4% of maltose and 1% of peptone; and YpSs medium containing 1.5% of soluble starch, 0.4% of yeast extract, 0.1% of potassium secondary phosphate, 0.05% of heptahydrate of magnesium sulfate. By cultivating in one of these media under an aereobic condition, the monomethylamine-oxidizing enzyme can be manufactured. With any medium, it is preferable to conduct cultivation in the presence of sufficient oxygen. For this purpose, shaking culture or stirring-with-aeration culture is employed.

Cultivating conditions are generally 20° to 35° C., pH 6 to 8 and 10 hr. to 7 days.

In solid culture, there are used solid media such as (a) bran media prepared by spraying water on commercial brans in a quantity of 60 to 80% by weight based on bran, (b) media prepared by appropriately adding to the above bran media carbon sources, nitrogen sources and small quantity ingredients which are assimilated by the present strain, (c) pelletized media of proper size and shape prepared from the media (a) or (b), etc.

Cultivating conditions are generally 20° to 35° C., pH 6 to 8 and 1 to 10 days.

By cultivating bacteria producing the monomethylamine-oxidizing enzyme in the above mentioned methods and conditions, the monomethylamine-oxidizing enzyme can be manufactured.

Collection of the monomethylamine-oxidizing enzyme from the culture mixture may be conducted directly from the filtrate of the liquid culture mixture or from the water extract of the solid culture mixture. However, since this enzyme is not easily secreted outside bacterial cells, the enzyme inside the cells can be more efficiently collected by collecting bacterial cells from the culture mixture and suspending these cells in an appropriate buffer solution and then destructing the cells by the use of ultrasonic treatment, surfactant treatment such as Triton X-100 (non-ionic synthetic surfactant manufactured by Rohm and Haas Co.), mechanical grinding or bacteriolytic enzyme such as lysozyme.

The crude enzyme solution thus obtained is subjected to nucleic acid removal prior to its purification. Nucleic acid is removed from the crude enzyme solution, either by adding to the solution if necessary protamine, manganese chloride, ethyleneimine polymer, etc. to precipitate the nucleic acid or by adding nuclease to decompose the nucleic acid. Subsequently, the nucleic acid-removed enzyme solution is purified by the use of an appropriate method selected from various known methods such as (a) salting-out method using ammonium sulfate, sodium sulfate, sodium chloride, etc., (b) precipitation method using an organic solvent such as an acetone or an alcohol, (c) gel filtration chromatography using TOYOPEAL HW-55S, TOYOPAEL TSK-55S (manufactured by Toyo Soda), Sephadex G 200, Sepharose 6B (manufactured by Pharmacia Co., Sweden), Biogel P 300 (manufactured by Bio-Rad Laboratories, U.S.A.), etc., (d) affinity chromatography using ω-aminohexyl agarose (manufactured by Miles Laboratories, Inc.), (e) adsorption chromatography using Hydroxyapatide (manufactured by Bio-Rad Laboratories, U.S.A.), (f) column chromatography using an ion exchanger such as Diethyl aminoethylsephadex (manufactured by Pharmacia Co., Sweden), Diethylaminoethylcellulose, Triethylaminocellulose (manufactured by Bio-Rad Laboratories, U.S.A.), etc., (g) electrofocusing method using Ampholine (manufactured by LKB, Sweden), etc., (h) electrophoretic method using acetate membrane, starch, acrylamide gel, etc., (i) dialysis method, (j) fractionation method using various membranes and (k) appropriate combinations thereof. Thus, a standard product of purified monomethylamine-oxidizing enzyme being homogeneous electrophoretically can be obtained.

Next, the quantitative determination method of monomethylamine using the monomethylamine-oxidizing enzyme provided by the present invention will be described.

Monomethylamine is industrially a useful compound which is used for tanning in the leather industry and for introduction of methyl group in the organic synthesis industry. Meanwhile, the compound may be hazardous to human body and is formed associated with decomposition of amino acids during the process of putrefaction of foods. Accordingly, in the food industry, the quantitative determination of monomethylamine is not only important from the hygenic standpoint but also provides a means to predict the extent of putrefaction of foods. In the clinical chemistry, the content of monomethylamine in urine and feces provides a means to examine the condition of Enterobacteriaceae as well as the abnormality of metabolism of nitrogen compounds.

Hence, the quantitative determination of monomethylamine is highly important for (a) manufacturing control in leather and organic synthesis industries, (b) examination of safety of foods and (c) diagnosis of abnormality in a living body.

There are various conventional methods for determining monomethylamine in samples, however, all of these conventional methods have some defects. For instance, the method in which monomethylamine is converted to a 2,4-dinitrophenyl derivative and then the derivative is subjected to paper chromatography [A.M. Asatoor; J. Chromatogr., Vol. 4, p 144, 1966] and the method according to gas chromatography [S.R. Dunn et al.; Anal. Chem., Vol. 48, p 41 to 44, 1976] are very complicated in procedure. Also, there are mentioned the method in which monomethylamine is reacted in an alkaline state with an aqueous TNBS (sodium 2,4,6-trinitrobenzenesulfonate) solution and the color developed is colorimetrically determined at 420 nm [T. Okuyama et al.; J. Biochem., Vol. 47, p 454, 1960], the method in which monomethylamine is reacted with ninhydrin reagent in citric acid buffer solution (pH 5) at an elevated temperature and the developed color is colorimetrically determined at 570 nm [E. Yemm et al.; Analyst, Vol. 80, p 209, 1955] and the method in which a primary amine is allowed to develop fluorescence by the use of o-phthalaldehyde and the fluorescence intensity is measured at an exciting wave length of 340 nm and a fluorescence wave length of 455 nm [M. Roth; Anal. Chem., Vol. 43, p 880, 1971]. These methods all have no specificity to monomethylamine and are poor in precision, and accordingly need to be combined with paper chromatography, gas chromatography or ion exchange chromatography, which results in complicated procedure. Besides, the method using methylamine dehydrogenase [R.R. Eady et al.; Biochem. J., Vol. 106, p 245 to 255, 1968] requires additionally phenazine methosulfate and 2,6-dichlorophenolindophenol reagents as electron acceptors.

In view of the above situation, the present inventors made various studies and, as the result, found that monomethylamine can be quantitatively determined by a very simple procedure, in a short period of time and with an extremely high sensitivity by allowing the monomethylamine-oxidizing enzyme of this invention to act upon a sample of which monomethylamine content is to be quantitatively determined and by measuring the quantity of formaldehyde, ammonia or hydrogen peroxide formed.

That is, according to this invention, there is further provided a method for quantitatively determining monomethylamine contained in a sample, which method is characterized in that the monomethylamine-oxidizing enzyme is allowed to act upon a sample of which monomethylamine content is to be determined and then the quantity of formaldehyde, ammonia or hydrogen peroxide formed is measured.

Hereunder, the method for quantitatively determining monomethylamine will be explained in detail.

In the present invention, the sample for monomethylamine determination can be any material so long as it contains monomethylamine. There may be mentioned, for instance, foods such as meat and fish, feces, urine, monomethylamine-containing liquids obtained by allowing a methylguanidine-decomposing enzyme to act upon methylguanidine-containing samples, etc.

When the above samples contain considerable quantities of solid matters, they are preferably used as extracts obtained by converting the samples into ground matters with a grinder or into slices with a slicer and if necessary further homogenizing these ground matters or slices with a homogenizer and subsequently subjecting these deformed samples to extraction with cold or hot water, etc.

pH of the sample may not be adjusted, however, it is desirable that the pH be adjusted to 5 to 10 and preferably 6 to 9 by the use of an appropriate pH adjusting agent such as hydrochloric acid, sulfuric acid, nitric acid, sodium hydroxide or potassium hydroxide.

The above sample is used for quantitative determination of monomethylamine as it is or after being diluted to an appropriate concentration with water, a buffer solution, etc.

Then, the monomethylamine-oxidizing enzyme is allowed to act on the above prepared sample to decompose monomethylamine into formaldehyde, ammonia and hydrogen peroxide.

The quantity of the monomethylamine-oxidizing enzyme to be added to the sample for quantitative determination of monomethylamine is appropriately adjusted depending upon the monomethylamine content in the sample, reaction conditions, etc.

The monomethylamine-oxidizing enzyme is allowed to act upon the sample at a temperature of 20° to 60° C. and preferably 30° to 50° C. At this temperature, the mixture is subjected to enzymatic reaction for a period enough to decompose monomethylamine and preferably for 5 to 60 min. while the mixture is being left standing or being stirred, whereby monomethylamine is decomposed into formaldehyde, ammonia and hydrogen peroxide. At this time, the monomethylamine-oxidizing enzyme may be immobilized to a carrier such as agarose, carrageenan, etc. or to a film such as nylon film, cellophane film, etc. by the use of known methods and be used as an immobilized enzyme column or an immobilized enzyme film.

Then, the content of formaldehyde, ammonia or hydrogen peroxide is measured by respective known methods. When the sample contains formaldehyde, ammonia or hydrogen peroxide prior to its mixing with the monomethylamine-oxidizing enzyme, their contents are measured beforehand by respective known methods and deducted from corresponding contents obtained after the reaction between the sample and the monomethylamine-oxidizing enzyme.

Formaldehyde may be measured by any method. For instance, there may be mentioned (1) the method in which aldehyde is reacted with acetylacetone reagent in the presence of an ammonium salt and diacetyldihydrolutidine formed is colorimetrically determined [T. Nash; Biochem. J., Vol. 55, p 416 to 421, 1953], (2) the method in which diacetyldihydrolutidine obtained in above (1) is subjected to fluorescence determination [S. Belman; Anal. Chim. Acta, Vol. 29, p 120 to 126, 1963], (3) the method in which formaldehyde is reacted with heating with sodium chromotropate in an acidic state by sulfuric acid and the color developed is colorimetrically determined [E. Samichi et al.; Anal. Chem., Vol. 34, p 1460 to 1464, 1962], (4) the method in which formaldehyde is reacted with the previously mentioned AHMT in an alkaline state and after oxidation with periodic acid the color developed is colorimetrically determined [R. G. Dickenson et al.; Chem. Comm., p 1719 to 1720, 1970] and (5) the method in which formaldehyde is oxidized with formaldehyde dehydrogenase and the formed NADH is colorimetrically determined [Z. B. Rose et al.; Methods in Enzymology, Vol. 9, p 357 to 360, 1966].

Ammonia may be measured by any method. For instance, there may be mentioned (1) the method using Nessler's reagent, (2) the method in which indophenol reaction is conducted and the color developed is colorimetrically determined and (3) the method using an ammonia electrode.

Hydrogen peroxide may be measured by any method. For instance, there may be mentioned (1) the method in which peroxidase is allowed to act upon hydrogen peroxide using o-dianisidine as a hydrogen donor and the color developed is colorimetrically determined [H. Paul et al.; Clin. Chem., Vol. 16, p 427 to 430, 1970], (2) the method in which peroxidase is allowed to act upon hydrogen peroxide in the copresence of 4-aminoantipyrine and phenol and the color developed is colorimetrically determined [P. Trinder; Ann. Clin. Biochem., Vol. 6, p 24, 1969], (3) the method measuring the increase of absorbance at 240 nm [R.F. Beer et al.; J. Biol. Chem., p 195 and 133, 1952], (4) the method in which catalase is caused to act upon hydrogen peroxide in the presence of methanol and formaldehyde formed is measured and (5) the method in which catalase is allowed to act upon hydrogen peroxide and oxygen gas formed is measured by the use of a manometer or an oxygen electrode.

Next, it is necessary that a correlation between the quantity of formaldehyde, ammonia or hydrogen peroxide and O. D. value or relative fluorescence intensity be measured and, using the correlation, a standard calibration line be prepared. Hence, for the purpose of examining the correlation between the quantity of monomethylamine in sample and O. D. value, the following experiments were conducted.

EXPERIMENTAL EXAMPLE 1

Quantitative Determination of Monomethylamine by Reacting with Acetylacetone Reagent in the Presence of an Ammonium Salt and Colorimetrically Determining Diacetyldihydrolutidine Formed.

I. Preparation of Reagents (1) Monomethylamine-oxidizing enzyme solution

Two liters of a medium (pH 7.2) comprising 0.1% (w/v) (hereinafter "%" refers to "w/v" unless otherwise specified) of monomethylamine hydrochloride, 1% of glucose, 1% of yeast extract, 0.1% of potassium biphosphate, 0.05% of magnesium sulfate, 0.01% of ferrous sulfate, 0.01% of manganese chloride and water was introduced into the cultivating vessel of a small-sized fermenter with a stirrer (manufactured by Iwashiya) and sterilized under high pressure. The medium was inoculated with 20 ml of a bacterium suspension prepared by adding a sterilized physiological salt solution to a stored slant of *Bacillus* sp. N - 104 (FERM BP - 59), and then was subjected to aeration submerged culture with stirring at 30° C. for 48 hr.

The culture fluid thus obtained was centrifuged to collect wet bacterial cells. The cells were suspended in 400 ml of 2% Triton X-100 solution and subjected to bacteriolysis by allowing the suspension to stand at 30° C. for 1 hr.

Then, the precipitate was removed by centrifugation and there was obtained a supernatant (crude enzyme solution). This solution was salted out with ammonium sulfate of 0.5 saturation in the usual manner. The precipitate formed was collected and dissolved in 0.01 M phosphate buffer (pH 7.0) solution. The solution was dialyzed and desalted with the same buffer solution to obtain 180 ml of a monomethylamineoxidizing enzyme solution (enzymatic activity: 1.38 units/ml).

(2) Acetylacetone reagent 0.2% of acetylacetone was dissolved in 2 M ammonium acetate solution (adjusted to pH 6.0 by addition of acetic acid).

(b) Buffer solution 0.1 M phopshate buffer solution (pH 7.0)

(4) Monomethylamine solutions (standard solutions)

Monomethylamine hydrochloride was dissolved in the above buffer solution so that each 100 μl of the buffer solution contained the monomethylamine hydrochloride in quantities of 0.007, 0.015, 0.03, 0.06, 0.12, 0.23, 0.46 and 0.92 μmoles, respectively.

II. Measurement of Formaldehyde Formed from Monomethylamine

To each 100 μl of the monomethylamine solution (standard solution) prepared in I-(4), were added 100 μl of the above prepared monomethylamine-oxidizing enzyme solution and 1.8 ml of the above prepared buffer solution. After thorough mixing, the mixture was subjected to reaction by allowing to stand at 37° C. for 30 min.

Then, to the resulting reaction mixture was added 2 ml of the above-mentioned acetylacetone reagent. After thorough mixing, the mixture was subjected to color-developing reaction by allowing to stand at 37° C. for 40 min.

The colored solution thus obtained was subjected to fluorescence determination at an exciting wave length of 412 nm and a fluorescence wave length of 510 nm, for the case the monomethylamine solution having a monomethylamine content of 0.12 μmoles (120 nmoles) or below was used (see FIG. 5), and to colorimetric analysis at a wavelength of 412 nm, for the case the monomethylamine solution having a monomethylamine content of 0.03 μmoles or above was used (see FIG. 6).

The blank was measured by repeating just the same procedure as above, except that 100 μl of the buffer solution was used in place of 100 μl of the monomethylamine-oxidizing enzyme solution.

Figure 5:
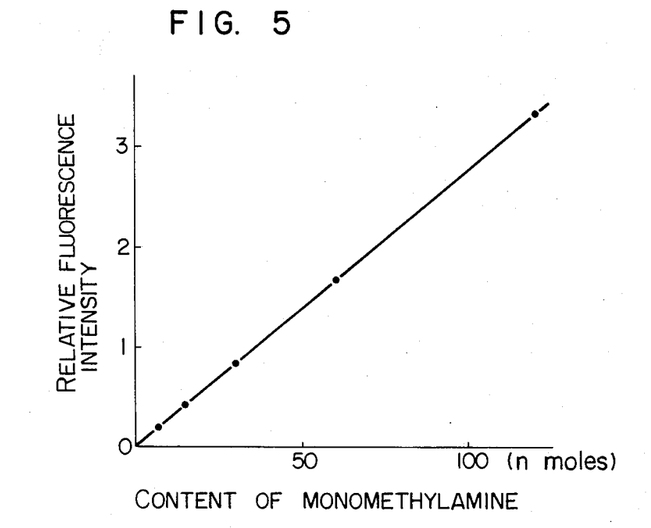
FIG. 5 is a graph (standard calibration line) showing the correlation between the quantity of monomethylamine and the relative fluorescence intensity value when produced formaldehyde is reacted with acetylacetone reagent in the presence of an ammonium salt and diacetyldihydrolutidine formed is subjected to fluorescent determination and colorimetric determination.

The value of blank was deducted from the value of the relative fluorescence intensity at 510 nm or from the O. D. value at 412 nm. Then, a correlation between the value of the relative fluorescence intensity after the deduction and the quantity of monomethylamine was obtained as shown in FIG. 5, and a correlation between the O. D. value after the deduction and the amount of monomethylamine was obtained as shown in FIG. 6.

Figure 6:
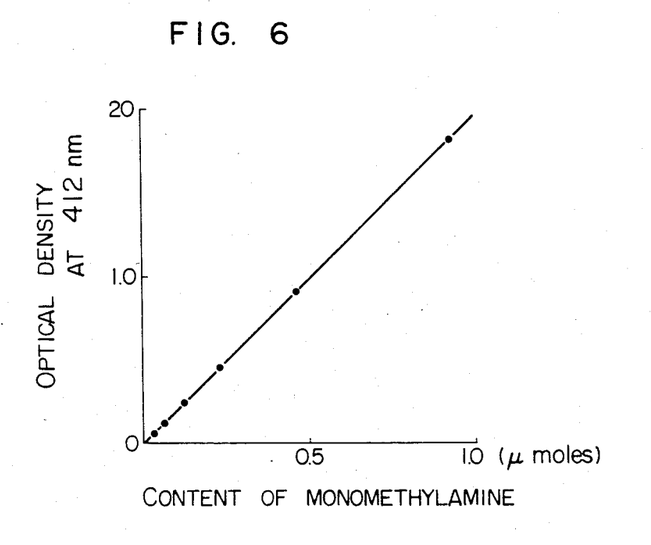
FIG. 6 is a graph (standard calibration line) showing the correlation between the quantity of monomethylamine and the O.D. value as measured in the same manner as in FIG. 5.

FIGS. 5 and 6 clearly demonstrate that there is a linear correlation between the quantity of monomethylamine and the value of the relative fluorescence intensity after the deduction or the O. D. value after the deduction and this correlation can be satisfactorily used as a standard calibration line.

The following experimental example relates to quantitative determination of monomethylamine comprising (1) allowing the monomethylamine-oxidizing enzyme to act upon a monomethylamine-containing solution, (2) reacting the resulting hydrogen peroxide with peroxidase in the presence of 4-aminoantipyrine and phenol and (3) colorimetrically determining the color developed.

EXPERIMENTAL EXAMPLE 2

I. Preparation of Reagents (1) Monomethylamine-oxidizing enzyme solution

The monomethylamine-oxidizing enzyme solution (enzymatic activity: 1.38 units/ml) obtained in Experimental Example 1 was concentrated to 10 times with a ultrafiltration system (Minimodule M-3 manufactured by Asahi Kasei K.K.). The concentrate was passed through a column packed with TOYOPEAL TSK-55S (manufactured by Toyo Soda) previously equilibrated with 0.01 M phosphate buffer solution containing 0.5 M KCl, to conduct high speed gel filtration chromatography. Then, the active fraction was collected, dialyzed against 0.01 M phosphate buffer solution containing 0.05 M KCl, and adsorbed onto ω-aminohexyl agarose (manufactured by Miles Laboratories, Inc.) previously equilibrated with the same buffer solution. After undesirable proteins had been completely washed out with the same buffer solution, affinity chromatography was applied with 0.01 M phosphate buffer solution containing 0.2 M KCl.

The active fraction thus obtained was dialyzed against distilled water and freeze-dried to obtain a standard product of purified monomethylamine-oxidizing enzyme (enzymatic activity: 18 units/mg).

0.5 mg of this product was dissolved in 5 ml of 0.1 M phosphate buffer solution to use as the monomethylamine-oxidizing enzyme solution.

(2) Buffer solution 0.1 M phosphate buffer solution (pH 7.0)

(3) 4-aminoantipyrine-phenol-peroxidase reagent (color-developing reagent)

16.2 mg of 4-aminoantipyrine and 131.7 mg of phenol were dissolved in 0.1 M phosphate buffer solution. Further, 1000 units (10 mg) of peroxidase (manufactured by Boehringer Mannheim, West Germany, ca. 100 units/mg) were dissolved therein. The total quantity was increased to 100 ml with the buffer solution.

(4) Monomethylamine solution (standard solution)

Monomethylamine hydrochloride was dissolved in the above buffer solution so that the content thereof in the solution became 0.036, 0.073, 0.146, 0.292, 0.584 and 1.168 μmoles per 100 μl of the solution.

II. Measurement of Hydrogen Peroxide Formed from Monomethylamine

To each 100 μl of the above prepared monomethylamine solution were added 1.8 ml of the above buffer solution and 100 μl of the above monomethylamine-oxidizing enzyme solution. The mixture was subjected to reaction while it was left standing at 37° C. for 20 min. To the reaction mixture was added 2 ml of the above 4-aminoantipyrine-phenol-peroxidase reagent. After thorough mixing, the mixture was subjected to color-developing reaction at 37° C. for 10 min. The developed color was colorimetrically determined at a wavelength of 500 nm.

The blank was measured by repeating just the same procedure as above, except that 100 μl of the buffer solution was used in place of 100 μl of the monomethylamine-oxidizing enzyme solution. (This applies also to Example 4 set forth later.)

This value of blank was deducted from the O. D. value at 500 nm obtained above. Then, a correlation between the O. D. value after the deduction and the quantity of monomethylamine was obtained as shown in FIG. 7.

Figure 7:
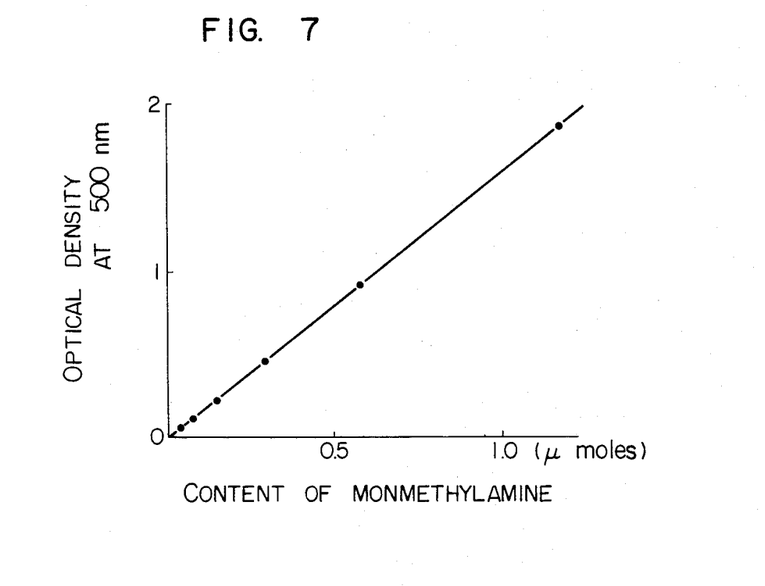
FIG. 7 is a graph (standard calibration line) showing the correlation between the quantity of monomethylamine and the O.D. value when peroxidase is allowed to act upon produced hydrogen oxide in the copresence of 4-aminoantipyrine and phenol and the color formed is colorimetrically determined.

FIG. 7 Clearly demonstrates that there is a linear correlation between the quantity of monomethylamine and the O. D. value after the deduction and the correlation can be satisfactorily used as a standard calibration line.

As is obvious from the above explanation, according to the present invention, monomethylamine can be quantitatively determined by a very simple procedure, in a short period of time and with a very high sensitivity and precision.

The following experimental example relates to quantitative determination of methylguanidine comprising (1) allowing the methylguanidine-decomposing enzyme to act upon a methylguanidine-containing sample, (2) allowing the monomethylamine-oxidizing enzyme to act upon the resulting reaction mixture (monomethylamine-containing solution) and (3) measuring formaldehyde formed.

EXPERIMENTAL EXAMPLE 3

I. Preparation of Reagents (1) Methylguanidine-decomposing enzyme solution

Two liters of a medium (pH 7.2) comprising 1.0% of glycerol, 0.2% of methylguanidine sulfate, 0.1% of disodium hydrogen phosphate, 0.1% of magnesium sulfate, 0.05% of yeast extract, 0.01% of ferrous sulfate, 0.01% of manganese chloride and water was introduced into the cultivating vessel of a small-sized fermenter with a stirrer (manufactured by Iwashiya) and sterilized under high pressure. The medium was inoculated with 20 ml of a seed bacterial solution of *Alcaligenes* N-243 (FERM P-4369, ATCC 31370) which had been cultivated for 48 hr. in a medium (pH 7.2) having the same composition as above. It was subjected to aeration submerged culture with stirring at 30° C. for 48 hr.

The culture fluid thus obtained was centrifuged to give 17 g of wet bacterial cells, and the resulting cells were suspended in 50 ml of 0.05 M Veronal buffer solution (pH 9.0), and the cells were destructed by means of an ultrasonic disintegrator (manufactured by Bronson Co.) for 10 min. while cooling with ice water.

Then the precipitate was removed by centrifugation, and there was obtained 48 ml of the supernatant (crude enzyme solution) (enzyme activity: 43.3 units/ml).

The crude enzyme solution was salted out with ammonium sulfate in the usual manner. The resulting precipitate fraction was dissolved into 25 ml of water and dialyzed against 0.05 M Tris-hydrochloric acid buffer solution (pH 8.0) to obtain a methylguanidine-decomposing enzyme solution (enzyme activity: 60.5 units/ml).

(2) Carbonate buffer solution.

0.1 M sodium bicarbonate-sodium carbonate buffer solution (pH 10.0)

(3) Monomethylamine-oxidizing enzyme solution.

This solution was prepared in the same manner as in Experimental Example 1.

(4) Acetylacetone reagent.

This reagent was prepared in the same manner as in Experimental Example 1.

(5) Buffer solution.

0.1 M Phosphate buffer solution (pH 7.0)

(6) Methylguanidine solution (standard solution)

Methylguanidine sulfate was dissolved into 0.1 M carbonate buffer solution (pH 10.0) so that the sulfate content in the solution became 0.0037, 0.0092, 0.0184, 0.0369 and 0.922 μmoles per 100 μl.

II. Procedure

To each 100 μl of the above methylguanidine solution) were added 0.4 ml of 0.1 M carbonate buffer solution and 10 μl of the above-mentiond methylguanidine-decomposing enzyme solution. The mixture was subjected to enzymatic reaction at 45° C. for 15 min. To the reaction mixture were added 1.4 ml of 0.1 M phosphate buffer solution (pH 7.0) and 100 μl of the above-mentioned monomethylamine-oxidizing enzyme solution, and the mixture was subjected to enzymatic reaction at 45° C. for 15 min. To the resulting reaction mixture was added 2 ml of acetylacetone reagent. After thorough stirring, the solution was subjected to color-developing reaction at 45° C. for 20 min. The resulting colored solution was subjected to fluorescence determination at an exciting wavelength of 415 nm and a fluorescence wavelength of 510 nm.

The blank was measured by repeating just the same procedure as above, except that 10 μl of 0.1 M carbonate buffer solution was used in place of 10 μl of the methylguanidine-decomposing enzyme solution.

This value of blank was deducted from the above obtained fluorescence intensity value at a fluorescence wavelength of 510 nm. Then, a correlation between the relative fluorescence intensity value after the deduction and the quantity of methylguanidine was obtained as shown in FIG. 8.

Figure 8:
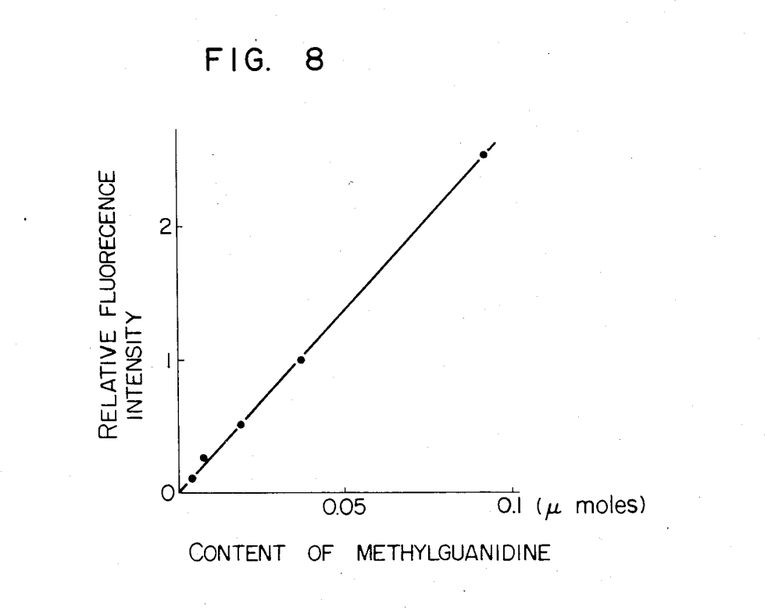
FIG. 8 is a graph (standard calibration line) showing the quantity of methylguanidine and the relative fluorescence intensity value when a methylguanidine-containing sample is reacted with a methylguanidine-decomposing enzyme, the monomethylamine-oxidizing enzyme is allowed to act upon the reaction mixture and formaldehyde formed is measured.

FIG. 8 clearly demonstrates that there is a linear correlation between the quantity of methylguanidine and the relative fluorescence intensity value and the correlation can be satisfactorily used as a standard calibration line.

Hereunder, this invention will be explained in more detail referring to Examples. However, it is not restricted by these Examples.

EXAMPLE 1

A seed bacterial solution ($10^9$ cells/ml) was prepared by adding a sterilized physiological saline solution to a stored slant of *Bacillus* sp. N - 104 (FERM BP-59) and making a suspension.

10 ml of the previously mentioned Medium A was placed in a large-sized test tube and sterilized at 120° C. for 30 min. under pressure. Then, it was aseptically inoculated with 0.5 ml of the above seed bacterial solution and subjected to shaking culture at 30° C. for 24 hr. The culture fluid thus obtained was centrifuged to collect wet bacterial cells. Then, these cells were suspended in 2 ml of 0.1 M phosphate buffer solution (pH 7.0) and the suspension was placed in an ultrasonic disintegrator for 4 min. with ice cooling to destruct cells. Subsequently, it was centrifuged and the supernatant was collected to obtain 1.8 ml of a crude enzyme solution (enzymatic activity: 0.29 units/ml).

EXAMPLE 2

Two liters of the previously metnioned Medium B (adjusted to pH 7.2) was introduced into the cultivating vessel of a small-sized fermenter with a stirrer having a three liter capacity (manufactured by Iwashiya) and sterilized at 120° C. for 30 min. under pressure. Then, the medium was aseptically inoculated with 20 ml of the seed bacterial solution prepared in Example 1 and subjected to aeration spinner submerged culture at 30° C. for 48 hr.

The culture fluid thus obtained was centrifuged to collect wet bacterial cells. The cells collected were suspended in 400 ml of 2% Triton X-100 (manufactured by Wako Junyaku) solution. The suspension was allowed to stand at 30° C. for 1 hr. for bacteriolysis and subsequently centrifuged to collect the supernatant. Thus, a crude enzyme solution was obtained.

Ammonium sulfate was added to this crude enzyme solution up to 0.5 saturation concentration to cause precipitation. This precipitate fraction was collected and dissolved into 0.01 M phosphate buffer solution (pH 7.0). The solution was dialyzed against the same buffer solution for desalting. Then, the dialyzate was condensed to 10 times with an ultrafiltration system (Minimodule M-3 manufactured by Asahi Kasei). The condensate was passed through a column packed with TOYOPEAL TSK-55S (manufactured by Toyo Soda) previously equilibrated with 0.01 M phosphoric acid buffer solution containing 0.5 M KCl, to conduct high speed gel filtration chromatography. The active fraction was collected and, after dialyzing against 0.01 M phosphate buffer solution containing 0.05 M KCl, adsorbed onto a column packed with $\omega$-aminohexyl agarose (manufactured by Miles Laboratories, Inc.) previously equilibrated with the same buffer solution. Undesirable proteins were completely washed out with the same buffer solution and then affinity chromatography was conducted with 0.01 M phosphate buffer solution containing 0.2 M KCl.

The active fraction thus obtained was dialyzed against distilled water and freeze-dried to obtain 7 mg of a standard product of purified monomethylamine-oxidizing enzyme (enzymatic activity: 8 units/mg). The optimum pH, pH stability, thermal stability and optimum action temperature range of this purified enzyme were shown in FIGS. 1, 2, 3 and 4, respectively. In FIG. 1, line-A, line-B, line-C, line-D and line-E show measurement results in 0.1 M $KH_2PO_4$-$Na_2HPO_4$ buffer solution, 0.15 M $KH_2PO_4$-$Na_2B_4O_7$ buffer solution, 0.15 M Veronal buffer solution, 0.1 M $H_3BO_4$-KCl-$Na_2CO_3$ buffer solution and 0.1 M $Na_2CO_3$-$NaHCO_3$ buffer solution, respectively. In FIG. 2, line-A, line-B, line-C and line-D show measurement results in 0.1 M acetate buffer solution, 0.1 M $KH_2PO_4$-$Na_2B_4O_7$ buffer solution, 0.1 M Veronal buffer solution and 0.1 M $Na_2CO_3$-$NaHCO_3$ buffer solution, respectively.

EXAMPLE 3

To 100 $\mu l$ of a monomethylamine-containing sample solution, were added 100 $\mu l$ of the monomethylamine-oxidizing enzyme solution prepared in Experimental Example 1 and 1.8 ml of the buffer solution prepared in Experimental Example 1. After thorough stirring, the mixture was subjected to reaction at 37° C. for 30 min. while it was left standing.

To the resulting reaction mixture was added 2 ml of acetylacetone reagent prepared in Experimental Example 1, and after thorough stirring, this mixture was subjected to color-developing reaction at 37° C. for 40 min. while it was left standing.

The resulting colored solution was subjected to colorimetric determination at a wavelength of 412 nm.

The blank was measured by repeating just the same procedure as above, except that 100 $\mu l$ of the buffer solution was used in place of 100 $\mu l$ of the monomethylamine-oxidizing enzyme solution.

By deducting the blank value from the above obtained O. D. value at 412 nm, the net O. D. value was calculated to be 0.832. By applying this value to the standard calibration line of FIG. 6, it was found that 100 $\mu l$ of the sample solution contained 0.425 $\mu$moles of monomethylamine.

EXAMPLE 4

To 100 $\mu l$ of a monomethylamine-containing sample solution were added 1.8 ml of the buffer solution prepared in Experimental Example 2 and 100 $\mu l$ of the monomethylamine-oxidizing enzyme solution prepared in Experimental Example 2. The mixture was subjected to reaction at 37° C. for 20 min. while it was left standing.

To the resulting reaction mixture was added 2 ml of 4-aminoantipyrine-phenol-peroxidase reagent prepared in Experimental Example 2. After thorough stirring, the mixture was subjected to color-developing reaction at 37° C. for 10 min., and the resulting colored solution was subjected to colorimetric determination at a wavelength of 500 nm.

By deducting the blank value from the above obtained O. D. value at 500 nm, the net O. D. value was calculated to be 0.098. By applying this value to the standard calibration line of FIG. 7, it was found that 100 $\mu l$ of the sample solution contained 0.062 $\mu$moles of monomethylamine.

EXAMPLE 5

To 100 $\mu l$ of a methylguanidine-containing sample solution were added 0.4 ml of 0.1 M carbonate buffer solution prepared in Experimental Example 3 and 10 $\mu l$ of the methylguanidine-decomposing enzyme solution. The mixture was subjected to enzymatic reaction at 45° C. for 15 min. To the resulting reaction mixture were added 1.4 ml of 0.1 M phosphate buffer solution (pH 7.0) and 100 $\mu l$ of the monomethylamine-oxidizing enzyme solution prepared in Experimental Example 1, and they were subjected to enzymatic reaction at 45° C. for 15 min. To the resulting reaction mixture was added 2 ml of acetylacetone reagent prepared in Experimental Example 1, and after thorough stirring, the mixture was subjected to color-developing reaction at 45° C. for 20 min. The resulting colored solution was allowed to stand at room temperature for 15 min. and then subjected to fluorescence determination at an exciting wavelength of 415 nm and a fluorescence wavelength of 510 nm.

By deducting the blank value from the above obtained relative fluorescence intensity value at 510 nm, the net relative fluorescence intensity value was calculated to be 1.75. By applying this value to the standard calibration line of FIG. 8, it was found that 100 $\mu l$ of the sample solution contained 0.063 $\mu$moles of methylguanidine.

What is claimed is:

1. A monomethylamine-oxidizing enzyme characterized by the following phyical and chemical properties:
   (a) having the ability to oxidatively deaminate the amino group of monomethylamine in the presence of water and oxygen to produce formaldehyde, ammonia and hydrogen peroxide;
   (b) having high substrate specificity for, in order of descending relative activity, monomethylamine, ethylamine, and n-propylamine;
   (c) having no substrate specificity for benzylamine, dimethylamine, trimethylamine, ethylenediamine and tyramine;
   (d) having a Km value toward monomethylamine of $6.2 \times 10^{-5}$ M at pH 9.0;
   (e) having an optimum of pH range for enzymatic activity of pH 8 to 9 and a stable pH range of enzymatic activity in the range of pH 6 to 9;
   (f) having optimum temperature ranges for enzymatic activity of (i) 40° to 50° C. at pH 7, and (ii) 30° to 40° C. at pH 9;
   (g) being inactivated at pH 7 when treated for 10 minutes at 70° C. or higher;
   (h) being inactivated at pH 9 when treated for 10 minutes at 63° C. or higher;
   (i) being completely inactivated at 30° C. and pH 3.0 or below;
   (j) being completely inactivated at 30° C. and pH 12 or higher,
   (k) having its activity inhibited at pH 9 when treated for 10 minutes at 30° C. in the presence of any of the compounds—concentrations selected from the group consisting of KCN (5 mM), 8-oxyquinoline (5 mM), o-phenanthroline (5 mM), sodium diethyldithiocarbamte (5 mM), $HgCl_2$ (1 mM), p-chloromercuribenzoic acid (1 mM), monoiodoacetic acid (1 mM), iodacetamide (1 mM), and semicarbazide hydrochloride (1 mM);
   (l) having its enzymatic activity stabilized by the addition of 2% (w/v) saccharose;
   (m) being electrophoretically uniform when subjected to electrophoretic measurement using a polyacrylamide gel; and
   (n) having a molecular weight of 320,000 as measured by gel filtration.

2. A monomethylamine-oxidizing enzyme according to claim 1, characterized by being obtained from a bacterium belonging to Genus *Bacillus*.

3. A monomethylamine-oxidizing enzyme according to claim 2, wherein te bacterium belonging to Genus *Bacillus* is *Bacillus* sp. N-104 (FERM BP-59).

4. A process for manufacturing a monomethylamine-oxidizing enzyme which comprises (a) cultivating in a medium a strain belonging to Genus *Bacillus* and having an ability to produce a monomethylamine-oxidizing enzyme and (b) collecting the monomethylamine-oxidizing enzyme from the culture mixture.

5. A process according to claim 4, wherein the strain belonging to Genus *Bacillus* is *Bacillus* sp. N-104 (FERM BP-59).

6. A process according to claim 4, wherein the medium contains carbon sources, nitrogen sources and small amount ingredients.

7. A process aocording to claim 6, wherein cultivation is conducted in a liquid medium aerobically at 20° to 35° C. at pH 6 to 8 for 10 hr. to 7 days.

8. A process according to claim 4, wherein monomethylamine hydrochloride is added to the medium in a quantity of 0.01 to 2% (w/v).

9. A method for quantitatively determining monomethylamine which comprises
   (a) allowing the monomethylamine-oxidizing enzyme of claim 1 to act upon a sample of which monomethylamine content is to be measured; and
   (b) measuring the quantity of formaldehyde, ammonia or hydrogen peroxide formed from the reaction.

10. A method for quantitatively determining monomethylamine according to claim 9, wherein the monomethylamine-oxidizing enzyme is an enzyme produced by a bacterium belonging to Genus *Bacillus*.

11. A method for quantitatively determining monomethylamine according to claim 9, wherein the bacterium belonging to Genus *Bacillus* is *Bacillus* sp. N-104 (FERM BP-59).

12. A method for quantitatively determining monomethylamine according to claim 9, wherein the sample of which monomethylamine content is to be measured is a monomethylamine-containing solution obtained by allowing a methylguanidine-decomposing enzyme to act upon a methylguanidine-containing sample.

13. A method for quantitatively determining monomethylamine according to claim 12, wherein the methylguanidine-decomposing enzyme is *Alcaligenes* N-243 (FERM P-4369, ATCC 31370).

14. A method for quantitatively determining monomethylamine according to claim 9, wherein the monomethylamine-oxidizing enzyme is allowed to act at 20° to 60° C. for 5 to 60 min.

* * * * *